United States Patent [19]

Grossman et al.

[11] 4,377,813
[45] Mar. 22, 1983

[54] ELECTROCARDIOGRAPH APPARATUS

[75] Inventors: Hyman Grossman, Buchanan; Claude MacQuignon, Lake Peekskill, both of N.Y.

[73] Assignee: Cambridge Instruments, Inc., Ossining, N.Y.

[21] Appl. No.: 240,510

[22] Filed: Mar. 4, 1981

[51] Int. Cl.³ .................. G01D 9/32; G01D 15/28; A61B 5/04
[52] U.S. Cl. .................. 346/33 ME; 346/136; 128/710
[58] Field of Search ............ 346/33 ME, 136, 145, 346/24, 34; 128/710

[56] References Cited

U.S. PATENT DOCUMENTS 3,082,970  3/1963  Rasmussen ............ 346/33 ME X
3,255,458  6/1966  Mellon .................. 346/108
4,184,487  1/1980  Peyer .................... 128/710

Primary Examiner—Stafford D. Schreyer
Attorney, Agent, or Firm—Eugene E. Geoffrey, Jr.

[57] ABSTRACT

Electrocardiographic apparatus including a novel and improved recording paper feed and lead switching arrangement which include a platen having a platen roller, both movable from an open position for installing a supply of recording paper to a position wherein the platen roller with recording paper fed about the surface thereof is moved to an operating position with the platen roller in recording engagement with a recording pen. A paper drive roller is positioned in adjoining relationship to the platen roller and engages the platen roller with the paper thereon when in the operating position. The recording paper is provided with spaced cue marks and transverse perforations between successive cue marks and the apparatus includes a cue detector and associated electric circuitry for detecting said cues so that heart muscle signals from successive groups of patient leads will be recorded on successive segments of the paper defined by the perforations.

7 Claims, 11 Drawing Figures

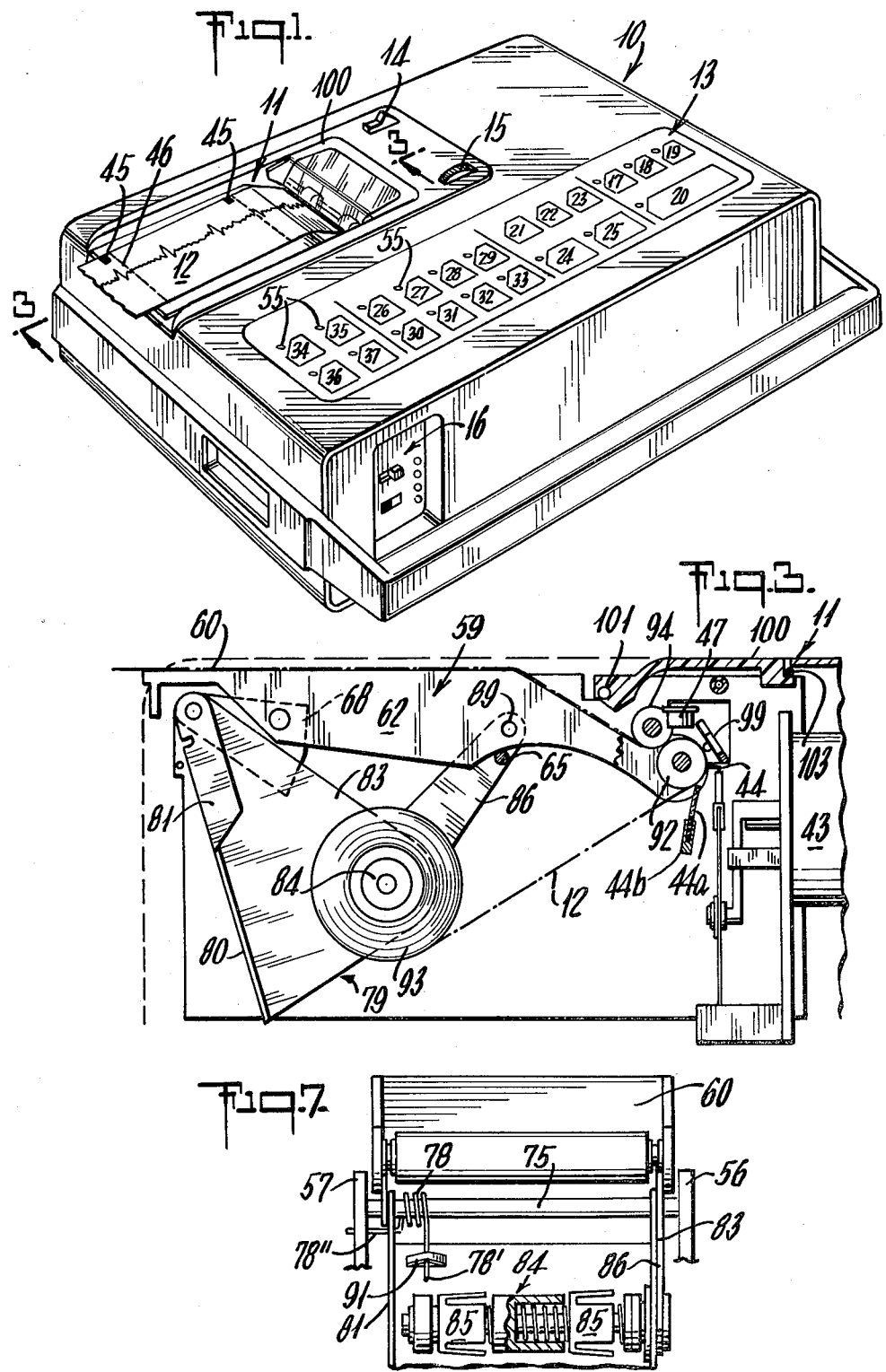

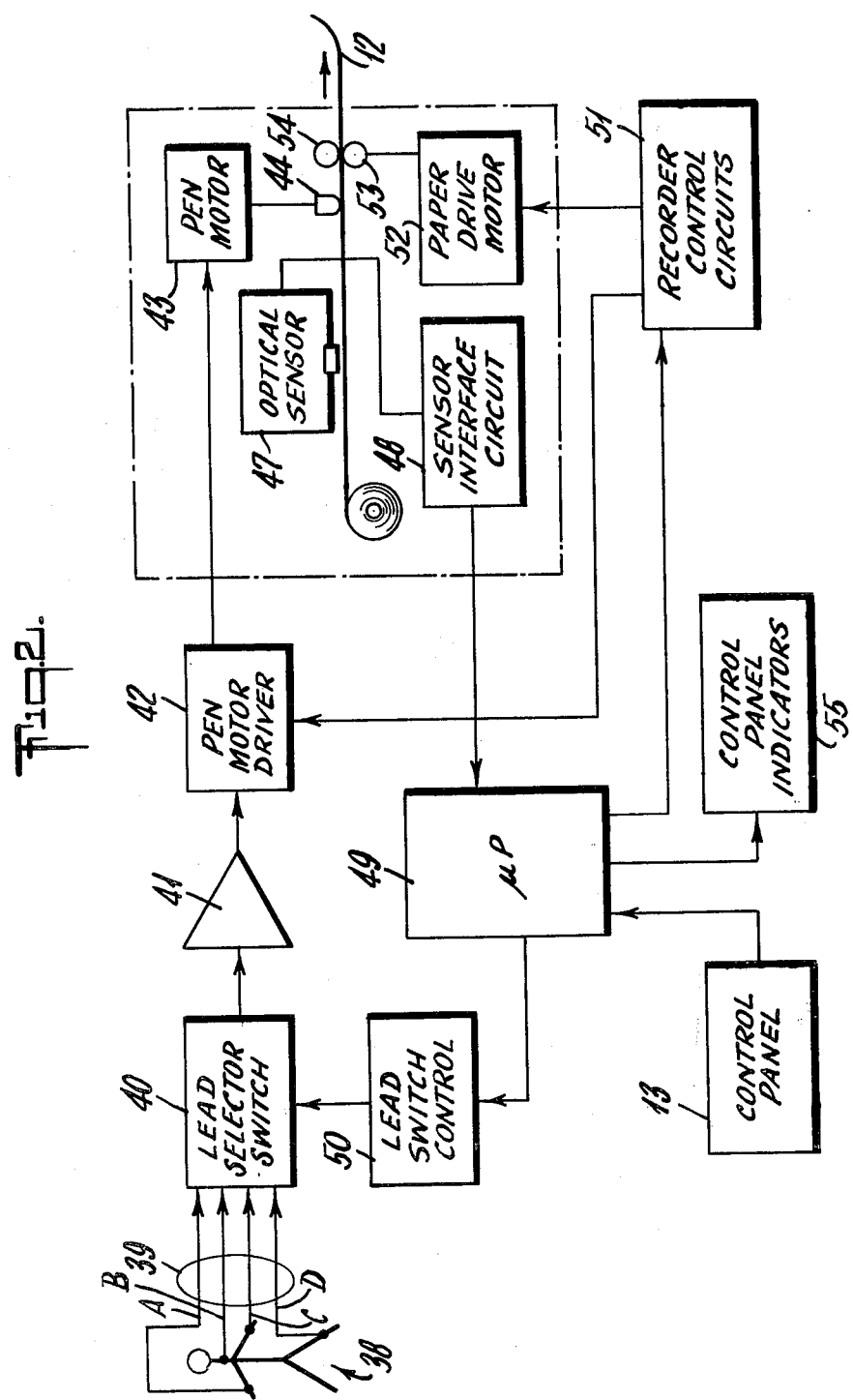

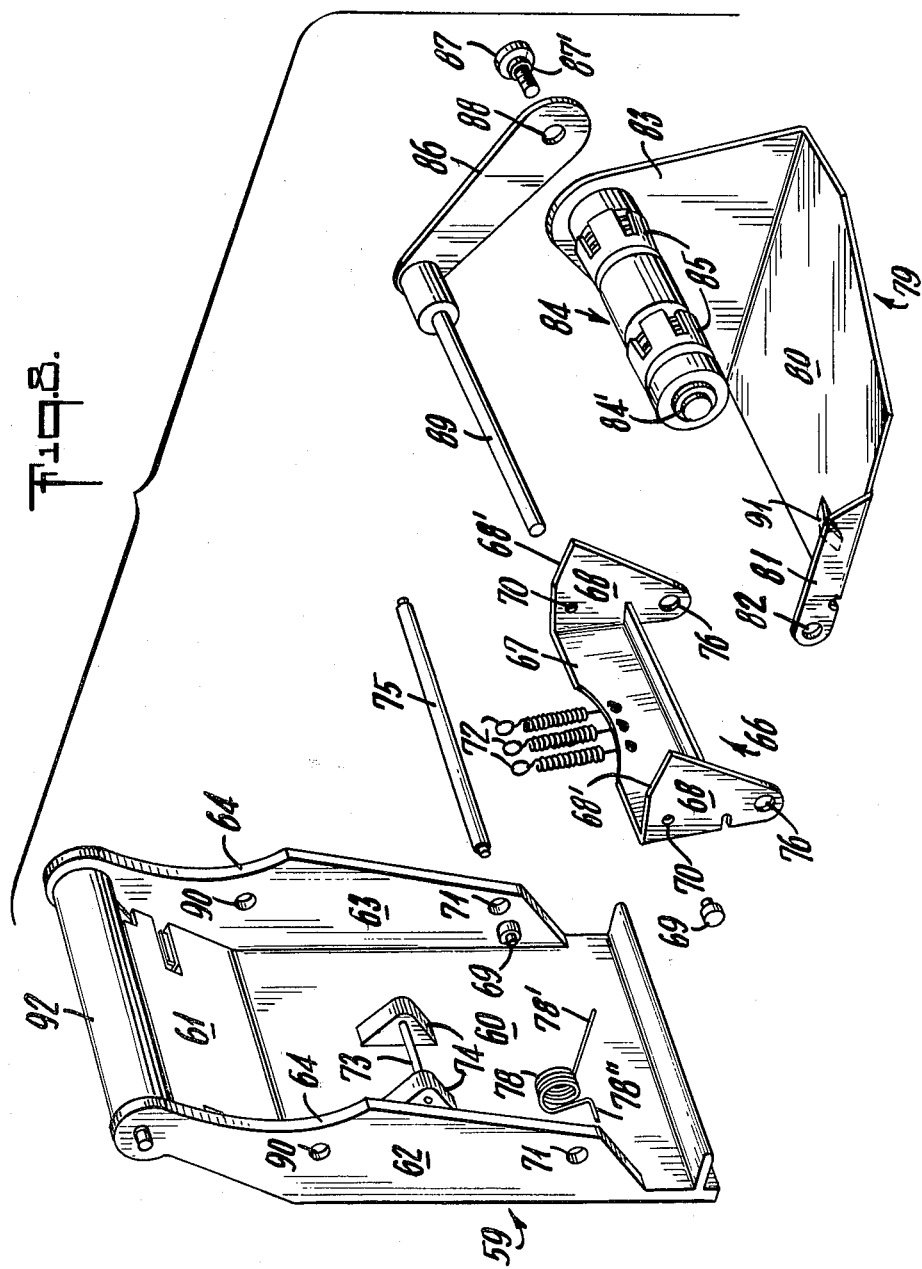

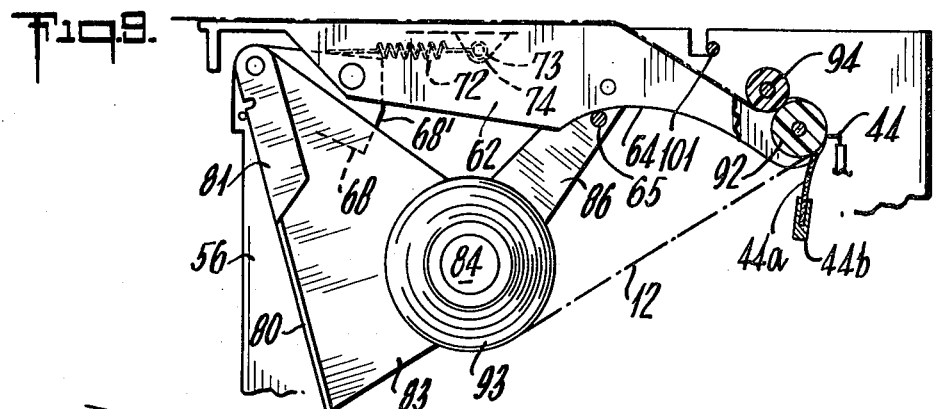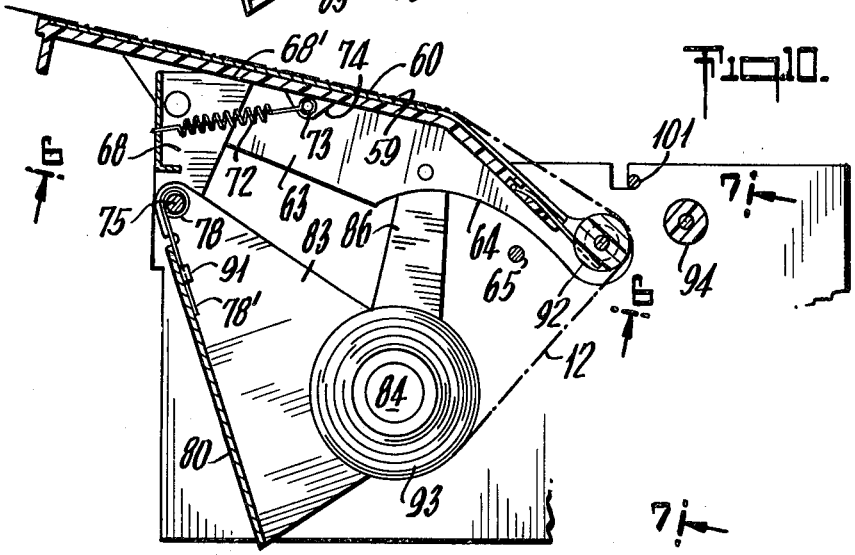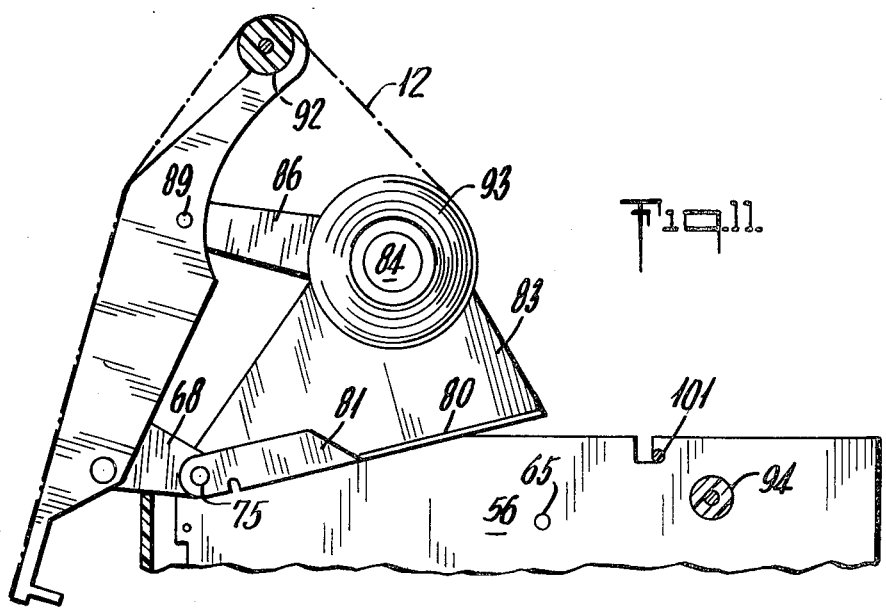

ELECTROCARDIOGRAPH APPARATUS

This invention relates to electrocardiographs and more specifically to novel and improved apparatus and recording medium or paper which are operatively related in a manner whereby the displacement of the paper during the recording process controls at least certain aspects of the recording procedure and to novel and improved paper feeding means insuring precise coordination of the paper with the apparatus.

Electrocardiographs for the detection and recording of electric current or voltage waveforms associated with the action of heart muscles are well known. Typical examples of known electrocardiographs are described in U.S. Pat. Nos. 3,922,686 and 4,050,079. Electrocardiographic recording procedures usually involve either a 12-lead system or a 15-lead system though the former is utilized more generally. In either case, different groups of leads are either successively or simultaneously recorded and automatic and semi-automatic systems have been utilized. In such cases, timing means operated by a suitable clock have been employed and upon completion of the recording procedure, it was necessary to carefully inspect the record and separate it into sections with each section properly identified for the specific lead combination. Such a procedure is necessarily tedious and time consuming.

This invention while principally directed to a single channel recorder may also be utilized in mutlichannel applications. It provides a novel and improved system wherein the recording paper is coordinated with and controls certain aspects of the operation of the recorder in both automatic and semi-automatic modes. By reason of the improved recording paper design, each successive lead combination which has been recorded is identifiable and the record is readily separable into discrete sections each including the recording of a specific lead combination. In addition, the apparatus includes novel and improved paper feeding means which simplifies the installation of the paper rolls and at the same time prevents the possibility of accidental damage to the recording pens and timing means which must cooperate with the paper.

Accordingly, one object of the invention resides in the provision of a novel and improved electrocardiograph including recording paper and paper feeding means which facilitates installation of the paper and wherein the paper upon being transported automatically controls the operation of the recorder to provide recordings on readily identifiable successive paper sections.

Still another object of the invention resides in the provision of a novel and improved electrocardiograph recorder and method of operation which is characterized by its simplicity, ease of operation and precise coordination of the recording paper with the recording apparatus.

A further object of the invention resides in the provision of novel and improved paper loading and feeding means for electrocardiographic recorders.

A still further object of the invention resides in the provision of a novel and improved electrocardiographic recorder.

The electrocardiographic apparatus in accordance with the invention utilizes an improved electronic control system coordinated with and controlled by the transport of the recording paper to achieve recordings of successive lead combinations on successive sections of the recording paper. These ends are attained by providing transverse perforated portions at predetermined points along the length of the paper and signalling means or cues carried by each perforated section of the record and precisely positioned relative to the perforations for cooperation with a fixed sensor. When the sensor senses the presence of a cue, the apparatus, depending upon its mode of operation, will automatically shift the recorder to the next successive lead combination. The next successive lead combination is then recorded when in the automatic mode or if in the semiautomatic mode the transport of the record is terminated until an appropriate signal is received from the operator to continue the recording. The apparatus further includes an improved paper feed which provides a paper transport system movable to a position away from the recording pens and sensor so that the paper can be placed in position and then moved into the recording position. In this way, accidental damage to the recording pens and sensor is effectively prevented.

The above and other objects and advantages of the invention will become more apparent from the following description and accompanying drawings forming part of this application.

IN THE DRAWINGS

FIG. 1 is a perspective view of an electrocardiograph in accordance with the invention;

FIG. 2 is a block diagram of the circuitry of the electrocardiograph of FIG. 1 and illustrating its cooperation with the recording paper;

FIG. 3 is a cross-sectional view of the paper feeding apparatus taken along the line 3—3 of FIG. 1;

Figure 6:
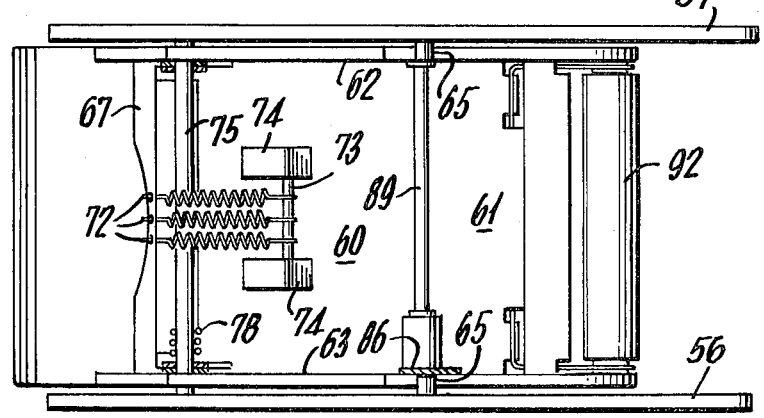

FIGS. 6 and 7 are cross-sectional views of FIG. 10 taken along the lines 6—6 and 7—7 thereof;

FIG. 8 is an exploded perspective view of the paper feeding mechanism; and

FIGS. 9, 10 and 11 are cross-sectional views similar to FIG. 3 in partially diagrammatic form illustrating steps in the operation of the paper feeding mechanism to install a roll of paper preparatory to the recording operation.

The electrocardiographic apparatus in accordance with the invention is illustrated in FIG. 1 and is denoted by the numeral 10. The apparatus includes paper feeding apparatus 11 with the recording paper 12 showing a simulated recording of a heart muscle wave form, a control panel 13, a power switch 14 and stylus centering control 15. Suitable provision is made for attachment of an AC power cable, cables for attachment to the patient, auxiliary outputs and controls 16 for modification of chart speed, frequency response and the like. The control panel 13 includes control elements 17, 18 and 19 for manual, semi-automatic and automatic operation, control element 20 to control the recording operation, control elements 21, 22 and 23 for applying a one millivolt calibration pulse to the record, applying identification marks to the record and inserting a reset pulse for re-establishing the base line. Control elements 24 and 25 are for interrupting the recording operation and observing the response of a patient preparatory to the recording operation. Control elements 26 through 33 permit the selection of specific lead combinations and control elements 34 through 37 provide for modification of the recording sensitivity in millimeters per millivolt. While the control elements 17 through 37 may take any suitable form such as push-buttons or the like, in the instant embodiment of the invention they are in the form of sensitive pressure operated switches so that extremely light pressure applied to any one of the elements will produce the desired operational mode. Control elements 17 to 20 and 24 to 37 each include an associated indicator light to inform the operator of the operational mode of the equipment at all times.

A block diagram illustrating the electronic circuitry of the recording apparatus in accordance with the invention together with the coordination of the circuitry with the transport of the recording medium, such as the recording paper 12, is illustrated in FIG. 2. In this diagram, the patient is denoted by the numeral 38 and the plurality of leads or cables 39 are connected from the patient to a lead selector switch 40 constituting in effect the input to the recording apparatus. Normally, four leads A, B, C and D are connected from the patient to the lead selector switch and signals from selected combinations of the leads 39 are recorded. Also, a fifth lead is usually connected to the patient as a reference but is not used in the formation of the signals to be recorded. Thereafter, a series of recordings are utilized with the lead B being placed at different positions on the patient's chest. This is the well known twelve-lead system and a detailed description is not deemed necessary. The output of the lead selector switch is fed through an amplifier 41 to the pen motor driver 42. This driver develops a sufficient power to drive the pen motor 43 and pen 44 which records the heart muscle wave form on the recording paper 12 as the latter is transported.

The recording paper 12, such as a heat sensitive paper or the like, is provided with a plurality of cue-marks 45 each in the form a of black rectangle and a transverse perforation 46 following each cue-mark as shown more clearly in FIG. 1. The cue-marks 45 function in combination with sensing means to shift leads from the patient automatically so that the recording appearing on the record between successive perforations constitutes the heart muscle wave forms recorded from that selected set of leads. More specifically, this end is attained through the utilization of the optical sensor 47 comprising a light source and light detector as shown in FIG. 2. When light normally reflected by the paper onto the detector is interrupted by reason of the presence of the black cue-mark, a signal is fed through the sensor interface circuit 48 and thence to the microprocessor 49. The microprocessor 49 receives information from the control panel 13 as well as from the sensor interface circuit 48 and transmits information to the lead control switch 50 which automatically controls the lead selector switch 40. Information from the microprocessor 49 is also fed to the recorder control circuits 51 to control the operation of the paper drive motor 52 which functions through the rollers 53 and 54 to affect transport of the paper on which the recordings are made. The recorder control circuits 51 also control the operation of the pen motor driver to effect its operation when the paper drive motor is activated. The microprocessor also feeds information to the control panel indicators previously described in order to inform the operator of the operational mode of the equipment at any given time.

As pointed out above, the apparatus will operate in either manual mode, semi-automatic mode or automatic mode. In the automatic mode, the apparatus will record successively six basic lead combinations which do not require movement of the chest electrode. Thereafter, the apparatus automatically shifts into a semi-automatic mode which consists of recordings made with the chest electrode at six different positions. This is the standard twelve-lead procedure which is well known in the art though in the case of this invention the first six lead combinations can be recorded automatically while the remainder are recorded semi-automatically. If desired, each lead combination including any of those that can be recorded automatically, can be recorded semi-automatically by merely depressing the semi-automatic switch prior to depressing the record switch in which case the apparatus will terminate recording after the completion of each recording segment between successive perforations 46 with the recording time being controlled by the optical sensor 47 and cooperating cue-marks 45. Manual recording is also possible. This is accomplished by pre-selecting the manual recording mode by depressing button 17 prior to depressing the record bottom 20. In this instance, the instrument will record continuously in the previously selected lead group until cancelled by pressing STOP or OBSERVATION buttons 24 or 25 respectively.

The feeding means for the recording medium or paper is shown in FIGS. 3 through 8. The feeding mechanism is denoted by the numeral 11 and includes a pair of side frame members 56 and 57 held in parallel relationship within the body of the recorder 10 and a transverse frame member 58 disposed between frame members 56 and 57 as shown more clearly in FIG. 4 carrying the pen motor 43 which drives the pen 44. A platen 59 having an upper wall 60 which is approximately coincident with the plane of the upper edges of the frame members 56 and 57 and an inclined portion 61 which slopes downwardly from the inner edge of the upper wall 60 toward the recording pen 44. The platen 59 also includes a pair of side wall members 62 and 63 each having an arcuate caming surface 64 which cooperates with a pin 65 carried by each of the side walls in a manner to be described in connection with FIGS. 9 through 11. The platen 59 is pivoted to the frame elements 56 and 57 by a platen support generally denoted by the numeral 66 as shown more clearly in FIG. 8. The platen support 66 includes a transverse member 67 having a pair of links 68 extending from the edges thereof to form an essentially U-shaped element. The platen support is pivotally secured to the platen by means of pins 69 engaging openings 70 in the platen support and cooperating openings 71 in the side walls 62 and 63 of the platen 59. A plurality of springs 72 are secured at one end to the platen support and at the other end to a rod 73 supported by a pair of brackets 74 depending from the top wall 60 of the platen 59. As will be shown, these springs function as a toggle and assist in retaining the platen in the open position as shown in FIG. 11 and in the closed position as shown in FIG. 9.

The platen and platen support assembly as described above is pivoted to the side frame elements 56 and 57 by a shaft 75 engaging openings 76 in the platen support links 68 and cooperating openings 77 in the frame elements 56 and 57 as shown more clearly in FIG. 7. In addition, a spring 78 surrounds the shaft 75 and engages the side wall 57 and the paper support assembly generally denoted by the numeral 79 to cause the platen to be moved to a counter-clockwise position as illustrated for instance in FIGS. 3 and 9 to 11. As will be shown, the spring 78 together with toggle springs 72 also operates to urge the platen roller 92 against the drive rollers 94.

The paper support 79 comprises a transverse plate 80, a flange 81 extending from one edge of the plate 80 and having an opening 82 therein and a second much deeper flange 83 carrying a paper holder generally denoted by the numeral 84. While the paper holder 84 may take any suitable form, in the instant embodiment of the invention it includes a pair of rollers 85 each having a plurality of spring fingers which grip the roll of recording paper to hold it in position thereon as shown in FIG. 3. The rollers 85 also frictionally engage the shaft 84' so that the paper 12 will be held taut as it is fed over the platen roller 92 during the recording operation. The paper holder or roller 84 together with the swing arm 86 is secured to the paper support member 83 by a screw 87 which threadably engages one end of the shaft 84'. The screw 87 has a shoulder 87' which rotatably engages an opening 88 in the swing arm 86 so that the swing arm can rotate relative to the member 83 forming part of the paper support. The swing arm includes an axle 89 on the outer end thereof which engages openings 90 in the side elements 62 and 63 of the platen 59. In addition, the transverse element 80 of the paper support includes a bracket 91 which engages the end portion 78' of the spring 78 while the end portion 78" of the spring 78 engages the frame portion 57 as previously described.

Figure 4:
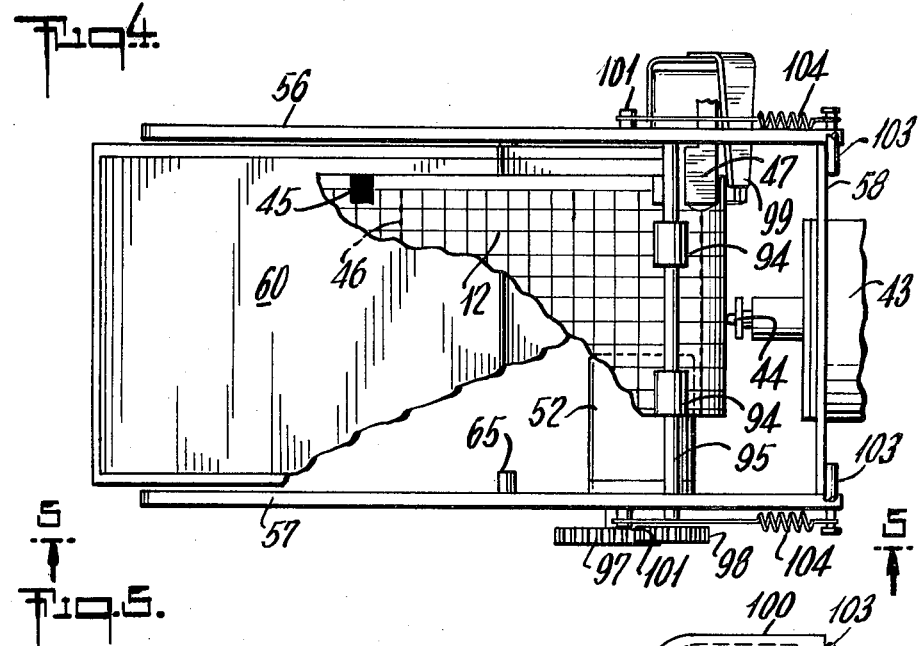
FIG. 4 is a top view of FIG. 3 with parts broken away and illustrating the recording paper.

The forward end of the platen 59 carries a spring-loaded platen roller 92 rotatably held by the side elements 62 and 63 of the platen 59. When the platen 59 is in the closed position as illustrated in FIGS. 3 and 9 and with a roll of recording paper 93 in position on the roller 84 as shown in FIG. 3, the end of the paper is drawn about the platen roller 92 and the paper will lie between the platen roller 92 and the pen 44 having a heated tip in order to effect the recording operation. The paper will also pass between the platen roller 92 and the drive roller 94 and thence upwardly over the surface 60 of the platen 59. The drive rollers 94, as shown more clearly in FIGS. 3 and 4, are carried by a shaft 95 rotatably carried by the side frame elements 56 and 57.

A paper drive motor 52 is carried on the inside of the frame element 57 and coupled through a gear train including gears 95 through 98 to rotate the drive rollers 94 upon being energized by the recorder control circuit 51. The optical sensor 47, which may take any desired form, is carried by the side frame element 56 as shown in FIGS. 3 and 4 and the sensor is aligned with the cue-marks 45 and functions to detect the presence of a cue-mark as the recording paper is transported. Upon sensing the cue-mark, a signal is transmitted through the sensor interface circuit 48 to the microprocessor 49 previously described. In addition, a second recording pen 99 having a heated tip is also carried by the frame element 56 and is aligned with the edge of the recording paper. Appropriate signals are fed to the pen 99 in order to identify the recording on each segment of the recording paper with the specific patient leads being recorded during that period of time. The pen 99 may also be used by the operator as an event marker to identify specific portions of the record during the recording operation for later consideration. Thus as each of the twelve-lead combinations is recorded on a record segment between successive perforations 46, each record segment is identified automatically by marker pen 99. The specific circuitry for operation of the marker pen 99 is well known in the art and accordingly additional description is not deemed necessary.

In the operation of the apparatus, both pens 44 and 99 are normally heated in order to effect the recording and marking. The heated portions of the pens however are formed of fine wire requiring a relatively short time to bring them up to operating temperature. In the case of pen 44, heating does not take place until the apparatus is activated so that it will not mark the record 12. Upon initiation of a recording, normal voltage is applied to the pen 44 which will bring the temperature of the pen to the normal recording temperature within about 200 milliseconds and at the same time paper transport is delayed about 200 milliseconds. In this way, recording, that is record transport, takes place only after the pen 44 is at the normal operating temperature. This procedure is desirable particularly in the case of battery operated apparatus as it reduces current drain to a minimum. The pen 99 is also brought to operating temperature each time recording is initiated but the pen is normally spaced from the record 12. Electromagnetic means, not shown, is used to move the pen into engagement with the record for lead identification and event marking.

Figure 5:
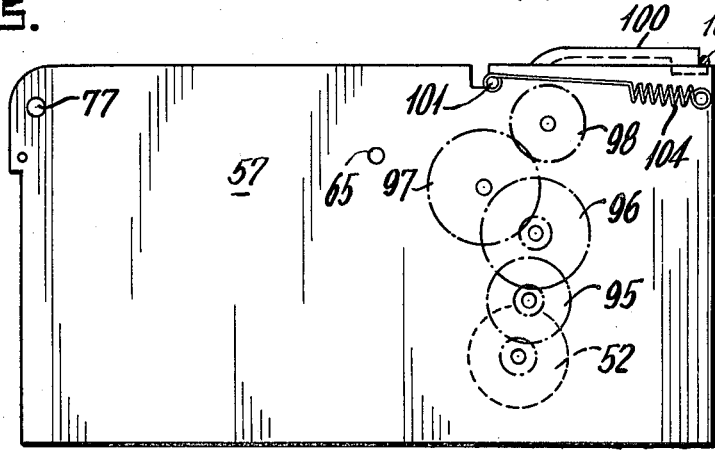
FIG. 5 is a side elevational view of the paper feeding mechanism taken in the direction of the arrows 5—5 of FIG. 4.

The paper feeding mechanism further includes a pen guard 100 as seen more clearly in FIGS. 3 and 5. This guard is preferably of a transparent material so that the operator can view the recording pen 44 for checking the operation of the equipment. Access to the recording pen 44, the optical sensor 47 and the marking pen 99 can be achieved by displacing the guard 100 to the left as viewed in the figures. More specifically, the guard is held in position by a pair of pins 101 carried in cooperating slots in the upper edges of the side frame members 56 and 57. The right hand end of the guard 100 includes a recessed end portion 102 which in the closed position underlies the pins 103. The guard is held in engagement with the pins 103 by a pair of springs 104 affixed at one end to the frame elements 56 and 57 and at the other end to the pivots 101. In this way by displacing the guard 100 to the left, it can be tilted upwardly to provide access to the pens.

As previously mentioned, when a roll 93 of paper is installed on the roller 84 and the paper is drawn over the platen roller 92, the platen is then moved to the operating position. However, the section of paper between the roll 93 and the platen roller 92 may not be drawn taut and may interfere with the recording operation. To avoid this difficulty, an elongated strip of felt or other suitable material 44a supported by a transverse channel 44b, as shown in FIGS. 3 and 9, is positioned below the pen 44 and bears firmly against the platen roller 92. With this arrangement and upon initiation of the recording process, the drive roller 94 will cause the paper 12 to tightly hug the platen roller 92 and slack, temporarily occurring between the platen roller 92 and the paper roll 93, will not affect the recording.

Referring now to FIGS. 9 through 11, it will be observed that the platen 59 is in a position wherein the platen roller 92 with the paper 12 in overlying relationship thereto is in firm engagement with the drive roller 94 and also in contact with the recording pen 44. It will also be observed that the springs 72 lie above the axis of the pivot pins 69 and function to hold the platen 59 in the forward position as illustrated and downwardly against the guide pins 65 which bear against the arcuate guides 64. This occurs by reason of the fact that the links 68 are in their full clockwise position as shown in these figures. Moreover, since the springs 72 urge the links in a clockwise direction, the platen 59 is urged forwardly and downwardly into contact with pins 65. Since the guides 64 are arcuate, they will urge the end of the platen upwardly into engagement with the drive rollers 94 so that the drive rollers will function to transport the paper 12. In as much as the platen roller 92 is spring loaded, such spring loading will control the pressure of the platen roller 92 against the drive rollers 94 and also compensate for differences in thickness of the recording paper.

To open the platen 59 for paper replacement or other purposes, the platen 59 is moved to the left as shown in FIG. 10. This is done by first lifting the left hand edge of the platen 59, as shown in the drawings, and then moving it to the left whereupon the arcuate guides 64 will move over the guide pins 65 causing the platen roller 92 to first move downwardly and then upwardly after it passes the drive roller 94. In FIG. 10, it will be observed that the links 68 have now moved to a substantially vertical position with the surfaces 68' in contact with the underside of the upper wall 60 of the platen 59. From this position, the spring 78 will function to rotate the platen assembly 59 and paper support assembly 79 in a counter-clockwise direction to the open position as shown in FIG. 11. In this position, the paper roll 93 is completely exposed to facilitate removal and replacement. Upon threading the paper about the platen roller 92, the entire assembly is rotated in a clockwise direction which brings the caming surfaces 64 into contact with the pins 65. Thereupon, the platen 59 is then merely moved to the right as shown in these figures to bring the platen roller 92 in engagement with the pen 44 and with the drive rollers 94.

It is apparent from the foregoing description of the paper feeding means that the novel and improved construction facilitates installation of paper and movement into operative position with the recording pens without the possibility of damaging the pens in any way. Furthermore, since the recording pens are in a protected position, they cannot be easily damaged during any reloading operation. Moreover, by reason of the interaction of the elements for forming the paper feeding mechanism, the operating position of the platen roller is automatically fixed to secure the desired pressure and at the same time adequate pressure of the platen roller against the drive roller is automatically effected in order to insure a positive uniform drive of the paper during a recording operation.

The term "recording paper" as used herein is intended to mean any suitable recording medium capable of recording displacement of a recording pen during transport of the medium.

While only one embodiment of the invention has been illustrated and described, it is apparent that alterations, changes and modifications may be made without departing from the true scope and spirit thereof.

What is claimed is:

1. Recording apparatus for electrocardiograph signals comprising a lead selector switch including means for the attachment of a plurality of leads from a patient, said switch including means sequentially selecting sets of leads in a selected order and feeding successive outputs to at least one output terminal, a recording medium in the form of an elongated paper strip or the like, a recording pen cooperating with said paper, means including a motor for feeding said paper past said pen during the recording operation, a pen drive motor, means connected to the output of said switching means and to said pen drive motor for recording signals appearing at the output of said switch, signalling cues carried at equally spaced intervals by said recording medium, sensing means for sensing the presence of each cue as it passes the sensing means during the recording operation and control means responsive to said sensing means and connected to said lead selector switch to operate the latter to feed the signals from the next successive set of leads to the pen motor each time a cue is sensed by the sensing means, said means for feeding said medium comprising a frame having a pair of spaced parallel plates, a platen disposed between and hinged at one end to one edge of said plates and movable from an open to an operating position, a platen roller rotatably carried at the other end of said platen, means depending from the underside of said platen and carrying a roller for supporting a supply of said recording paper, said recording pen being positioned at said other end of said frame and a recording paper drive roller carried between said plates in spaced relation to said pen, said platen when in the open position and with said recording paper being fed from said supply, about the platen roller and over the surface of said platen being displaceable relative to said frame to bring said platen roller with the recording paper thereon into operable contact with said pen and drive roller.

2. Recording apparatus according to claim 1 wherein said hinge includes a pair of spaced parallel links each having one end pivoted to one of said plates and the other end pivoted to said platen, a transverse member joining said links one to the other and toggle spring means between said platen and said transverse member, said spring means functioning when the platen is in the open position to bias said links toward said other end of said platen and when said platen is in the operating position to bias said links toward said one end of said platen and into engagement with said pen and drive roller, said links limiting the displacement of said platen toward said pen.

3. Recording apparatus according to claim 2 including a pair of inwardly extending guide pins carried by said plates, arcuate caming surfaces on the underside of said carriage for cooperation with said guide pins, said caming surfaces upon movement of the platen to said operating position engaging said guide pins and cooperating with said spring means to guide said platen roller to a position beneath said drive roller and then upwardly into engagement with said pen and said drive roller.

4. Paper feeding means for electrocardiographic apparatus having a recording pen for movement in a horizontal path comprising a pair of spaced parallel, vertically disposed plates forming a frame, a platen disposed between said plates and hinged at one end to one edge of said plates for movement from a closed, substantially horizontal operating position to a horizontally displaced, open position with an other end of said platen inclined upwardly, a platen roller carried at the other end of said platen, means underlying said platen and carrying means for supporting a supply of recording paper, the last said means being hinged to said one edge of said plates and carrying a link pivoted at one end to the last said means and at an other end to said platen, a recording paper drive roller carried between said plates in spaced relation to said pen and means for driving said paper drive roller, said platen when in said open position and with said paper being fed from said supply and over the surface of said platen roller being displaceable relative to said frame to bring said platen roller with the recording paper thereon into operable contact with said pen and drive roller.

5. Paper feeding means according to claim 4 wherein said hinge includes a pair of spaced parallel links each having one end pivoted to one of said plates and an other end pivoted to said platen, a transverse member joining said links one to the other and toggle spring means between said platen and said transverse member, said spring means functioning when the platen is in the open position to bias said links toward said other end of said platen and when said platen is in the operating position to bias said links toward said one end of said platen and into engagement with said pen and drive roller, said links limiting the displacement of said platen toward said pen.

6. Paper feeding means according to claim 5 including a pair of inwardly extending guide pins carried by said plates, arcuate caming surfaces on the underside of said carriage for cooperation with said guide pins, said caming surfaces upon movement of the platen to said operating position engaging said guide pins and cooperating with said spring means to guide said platen roller to a position beneath said drive roller and then upwardly into engagement with said pen and said drive roller.

7. Paper feeding means according to claim 6 including a strip of resilient material carried by and in transverse relationship to said plates, said strip being disposed in a substantially vertical plane below said pen with the upper edge portion in firm contact with the paper on said platen roller when said platen is in the operating position.

* * * * *